(12) United States Patent
Couderc et al.

(10) Patent No.: US 7,158,227 B2
(45) Date of Patent: Jan. 2, 2007

(54) LASER-INDUCED FLUORESCENCE ANALYSIS DEVICE AND SEPARATION APPARATUS COMPRISING SAME

(75) Inventors: François Couderc, Toulouse (FR); Michel Nertz, Sainte Foy d'Aigrefeuille (FR)

(73) Assignee: Picometrics S.A., Mongiscard (FR)

( * ) Notice: Subject to any disclaimer, the term of this patent is extended or adjusted under 35 U.S.C. 154(b) by 328 days.

(21) Appl. No.: 10/484,848

(22) PCT Filed: Jul. 22, 2002

(86) PCT No.: PCT/FR02/02611

§ 371 (c)(1),
(2), (4) Date: Jul. 22, 2004

(87) PCT Pub. No.: WO03/012409

PCT Pub. Date: Feb. 13, 2003

(65) Prior Publication Data

US 2004/0239924 A1 Dec. 2, 2004

(30) Foreign Application Priority Data

Jul. 25, 2001 (FR) .................................. 01 09956

(51) Int. Cl.
*G01N 21/64* (2006.01)
*G01J 3/33* (2006.01)

(52) U.S. Cl. ........................ 356/318; 356/72; 356/344; 250/458.1

(58) Field of Classification Search ................. 356/72, 356/318, 344; 250/458.1, 459.1, 461.1, 461.2
See application file for complete search history.

(56) References Cited

U.S. PATENT DOCUMENTS 6,008,055 A 12/1999 Zhu et al.

FOREIGN PATENT DOCUMENTS

DE  198 17 738  10/1999
WO  WO 00 04371  1/2000

OTHER PUBLICATIONS

Bruin G J M:, "Recent Developments in Electrokinetically Driven Analysis on Microfabricated Devices" Electrophoresis, Weinheim, DE, vol. 21, 2000, pp. 3931-3951, XP001031800, ISSN: 0173-0835, *p. 3939, colonne de droite, alinea 2-p. 3942, colonne de gauche, alinea 2* figures 4,6.

*Primary Examiner*—F. L. Evans
(74) *Attorney, Agent, or Firm*—Young & Thompson (57) ABSTRACT

A laser-induced fluorescence analysis device (1), comprising a tube (2) including a channel, elements projecting an excitation light (13), optical collecting member (7), optical measurement elements (8) and a processing member (9) for producing an analysis result, the collecting member being mechanically coupled to one end of the channel, the tube being integrally made of a material with refractive index either lower than that of water, or higher than both that of water and that of ambient air so as to guide the fluorescence light along the channel in the channel and/or its wall up to the collecting member, which is designed to collect the fluorescence light propagated along the longitudinal direction of the channel.

16 Claims, 4 Drawing Sheets

LASER-INDUCED FLUORESCENCE ANALYSIS DEVICE AND SEPARATION APPARATUS COMPRISING SAME

The present invention relates to a laser-induced fluorescence analysis device for producing fluorescence light from dissolved substances and for detecting this light for the purpose of chemical and biochemical analysis. The present invention also relates to a separation apparatus that includes such a device.

It is known to make laser-induced fluorescence measurements in order to identify and assay substances present in a solution, particularly in trace form. Such measurements have many applications, for example in biochemistry.

Document U.S. Pat. No. 6,011,882 discloses a chemical detector in which a tube made of a polymer known under the registered trademark Teflon A.F. 2400® is filled with an indicating reactant in liquid phase. The tube is exposed to a substance in vapor phase that it is desired to detect, which substance migrates through the wall of the tube thanks to the gas permeability of the material of which it is formed. The change of an optical characteristic of the indicating reactor upon contact with the substance in question is then detected. Described among the various detection techniques envisioned in that document are the detection of absorption and the detection of laser-induced fluorescence, which techniques use a light source that axially illuminates the inside of the tube from one of its ends and an optical fiber that axially collects the light at the other end of the tube in order to convey it to an analyzer. However, this arrangement is clearly more favorable to absorption detection since the waveguide properties of the Teflon tube conduct the light injected at the first end to the analyzer, so that, in the case of a fluorescence measurement, the analyzer receives a strong injected light signal superimposed on the fluorescence light signal to be detected, which very greatly degrades the sensitivity of the fluorescence measurement. Furthermore, this detector is not designed to work in conjunction with a separation system.

It is known that the sensitivity of fluorescence detection is increased by preventing the collection, at the same time as the fluorescence light, stray light and/or reflected or scattered excitation light. To avoid collecting excitation light, the document *Analytical Chemistry*, Vol. 72, No. 15, pp 3423–3430 (2000) and the document WO 00/04371 propose a capillary electrophoresis arrangement that uses a silica capillary coated on the outside with a layer of polymer having a refractive index lower than that of a separation medium filling the inside of the capillary, in which arrangement the capillary is illuminated in an orthogonal geometry, the direction of propagation of the excitation light being transverse to the capillary, whereas the fluorescence light is collected in the axial direction of the capillary. According to that document, the light that is emitted or scattered near the outer surface of the capillary propagates spirally along the entire length of the capillary, close to its outer surface, whereas the light emitted at the center of the capillary, such as the laser-induced fluorescence, statistically leaves the capillary near its center, thereby allowing the stray light at the detector to undergo spatial filtering. However, these documents remain silent about combining the analysis tube with a separation column or a discharge pipe of the separation system.

Document WO 96/15438 discloses another fluorescence detector in which the fluorescence light produced in an excitation region of a quartz tube is guided some distance away from the excitation region using a collector sleeve which must have a refractive index greater than that of the specimen occupying the inside of the tube and which is made of a material having essentially the same refractive index as the tube, said sleeve being fastened to the tube by melting, adhesive bonding, or molding. However, this detector has drawbacks insofar as the collector sleeve entails an additional cost and the interface between the collector sleeve and the tube ensuring optical contact is difficult to implement and/or is of limited effectiveness over time.

International application WO 00/60342 discloses a laser-induced fluorescence analysis device of the type comprising:
- a tube having a channel capable of containing a solution comprising at least one substance able to undergo a laser-induced fluorescence reaction;
- a projection means capable of projecting an excitation light beam on a portion of said channel in a direction making an angle of greater than 60° to a longitudinal direction of said channel, said excitation light being capable of inducing a fluorescence reaction in said substance or one of said substances;
- an optical collecting means placed so as to collect fluorescence light from said channel;
- an optical measurement means coupled to said collecting means so as to be able to measure said collected fluorescence light; and
- a processing means capable of processing a measurement signal transmitted by said measurement means in order to produce a result of the analysis of said solution.

More precisely, this known device comprises a capillary in which a solution to be analyzed, comprising a solute that becomes fluorescent under light excitation at a certain wavelength, is conveyed from a separation system, which may be a high-performance liquid chromatography (HPLC), a micro-high-performance liquid chromatography (µ-HPLC) or capillary electrophoresis (CE) system. A laser illuminates, perpendicular to the direction of the capillary, an analysis cell inside the capillary, the wavelength of the laser being chosen in order to excite the fluorescence of said solute. A ball-shaped lens is also provided for collecting fluorescence light from the analysis cell, a photomultiplier tube for measuring the collected fluorescence light and a means for analyzing the measurement signals produced by the photo multiplier tube in order to give a result of the analysis.

However, in that device the optical path of the excitation light and the optical path of the fluorescence light are partly collinear, so that a spectral filtering means, in the form of a dichroic mirror, is needed to separate them. However, such systems collecting fluorescence only in the excitation direction can collect only a small portion of this fluorescence emitted isotropically in space.

The object of the present invention is to provide a highly sensitive laser-induced fluorescence analysis device that can be combined with or included in a high-performance liquid chromatography, micro-high performance liquid chromatography, or capillary electrophoresis system and does not have the aforementioned drawbacks or some of them. The object of the invention is also to provide a separation and laser-induced fluorescence analysis apparatus.

To do this, the invention provides a laser-induced fluorescence analysis device comprising:
- a tube having a channel capable of containing a solution comprising at least one substance able to undergo a laser-induced fluorescence reaction, the material of said tube being substantially transparent to excitation light;
- at least one projection means capable of projecting an excitation light beam locally on a portion of said channel in a direction making an angle of greater than 60° to a longitudinal direction of said channel, said excitation light being capable of inducing a fluorescence reaction in said substance or one of said substances;

at least one optical collecting means placed so as to collect fluorescence light from said channel;

at least one optical measurement means coupled to said collecting means so as to be able to measure said collected fluorescence light; and a processing means capable of processing a measurement signal transmitted by said measurement means in order to produce a result of the analysis of said solution;

characterized in that a first collecting means is mechanically coupled to a first end of said tube, said tube being made of a material whose refractive index is either less than that of the water in the channel or greater than both that of the water in the channel and that of the air surrounding the tube, so as to be able to guide said fluorescence light along said channel in the channel and/or in the wall of the tube as far as said first collecting means, which collecting means is arranged so as to collect said fluorescence light propagating approximately along said longitudinal direction of the channel, and in that it includes a joining means for connecting, in operation, a second end of said tube to an output pipe of a separation system, so as to allow solution to flow and/or said substance or substances in said solution to be transported between said separation system and said tube, said tube having, at said second end, an internal wall of approximately conical, ellipsoidal or paraboloidal shape, one face of which is turned toward said first end and is capable of reflecting said fluorescence light toward said first end, said tube then having an internal cross section larger than that of said output pipe and constituting a fluorescence detection cell.

For the purpose of the invention, the water in the channel comprises essentially water (with a refractive index of about 1.33 for a wavelength of 488 nm) or water-miscible organic solvents, salts soluble in water, acids commonly used for transporting substances to be separated, or else a hydrogel (for example with a refractive index of about 1.36) or an electrolyte. For the purposes of the invention, the tube is capable of containing a stream or flow of liquid.

The advantage of a tube whose refractive index is less than that of the aqueous solutions and of most common solvents is that the index difference at the interface between the walls of the channel, having an index n, and the solution to be analyzed, having an index n', generates a high reflection coefficient, which reaches the value 1 (total reflection) in the case of light rays with a sufficient inclination to this interface. More precisely, if the angle of incidence of a fluorescence light ray generated in the solution inside the channel is determined by the angle θ between this ray and the vector perpendicular to the interface pointing toward the inside of the channel, the condition for total reflection of this ray is: $\theta \geq \arcsin(n/n')$.

The tube with its channel filled with solution to be analyzed therefore forms a waveguide with a liquid core capable of guiding the fluorescence light along its longitudinal direction with minute losses.

According to one particular feature of the invention, said tube portion locally illuminated by said excitation light beam is approximately adjacent to said joining means, so that said detection cell contains the region for exciting said substance or one of said substances.

Advantageously, the joining means is capable of joining the tube to the output pipe in a rigid and substantially contiguous manner.

Advantageously, the second end of the tube has, facing away from said face, an internal shoulder of cross section corresponding approximately to the external cross section of said output pipe and serving as a stop for that part of said output pipe fitted into the tube.

Advantageously, the internal cross section of said output pipe corresponds approximately to the internal cross section of the constriction defined between said shoulder and said face, at said second end of the tube.

Preferably, each collecting means comprises a waveguide, a hollow T-connector being placed between said waveguide and the corresponding end of the tube in order to connect them, one in the extension of the other, a side branch of said connector allowing said solution to flow and/or said substance or substances in solution to be transported toward or from the outside of said tube.

Advantageously, in capillary electrophoresis, said lateral branch of a first T-connector connects said first end of said tube to a reservoir, a first electrode being placed through a wall of said reservoir so as to be in contact with said solution, said solution being electrically conducting and in contact with a second electrode placed some distance from the first electrode, said electrodes being connected to a voltage source so as to establish an electrical potential difference between the two ends of the tube in order to make said substance or one of said substances migrate by electrophoresis, the waveguide associated with said first collecting means being connected via said first connector to said first end in the extension of the tube.

According to one particular feature of the invention, the side branch of a second hollow T-connector connects said second end of said tube to the aforementioned joining means, the waveguide associated with a second collecting means being connected via said second T-connector to said second end of the tube in the extension of the latter. In this case, said tube may also have, at said first end, an internal wall of approximately conical, ellipsoidal or paraboloidal shape, one face of which is turned toward said second end and is capable of reflecting said fluorescence light toward said second end.

According to another feature of the invention, the approximately conical (218), ellipsoidal or paraboloidal internal wall(s) of the tube (2, 202) is (are) coated with an oxidation-resistant reflective material (242).

Preferably, said tube has an internal diameter of up to 200 μm for use in capillary electrophoresis or μ-HPLC and up to 1000 μm for use in HPLC.

Preferably, the projection means comprises a light source placed laterally some distance from the channel and optical means placed between the light source and the channel in order to match the cross section of said excitation light beam to the inside diameter of said channel.

Provision may be made for the external wall of the tube to be coated with a reflective material, with the exception in particular of the wall portion facing the excitation region of the detection cell, which must remain transparent to the beam.

The invention also provides a chromatographic or electrophoretic separation apparatus which includes such an analysis device. In this case, the tube forms or is connected to a separation column of the apparatus.

The invention will be better understood, and other objects, details, features and advantages thereof will become more clearly apparent, over the course of the following description of several particular embodiments of the invention, given solely by way of illustration but implying no limitation, and with reference to the appended drawings. In these drawings.

Figure 1:
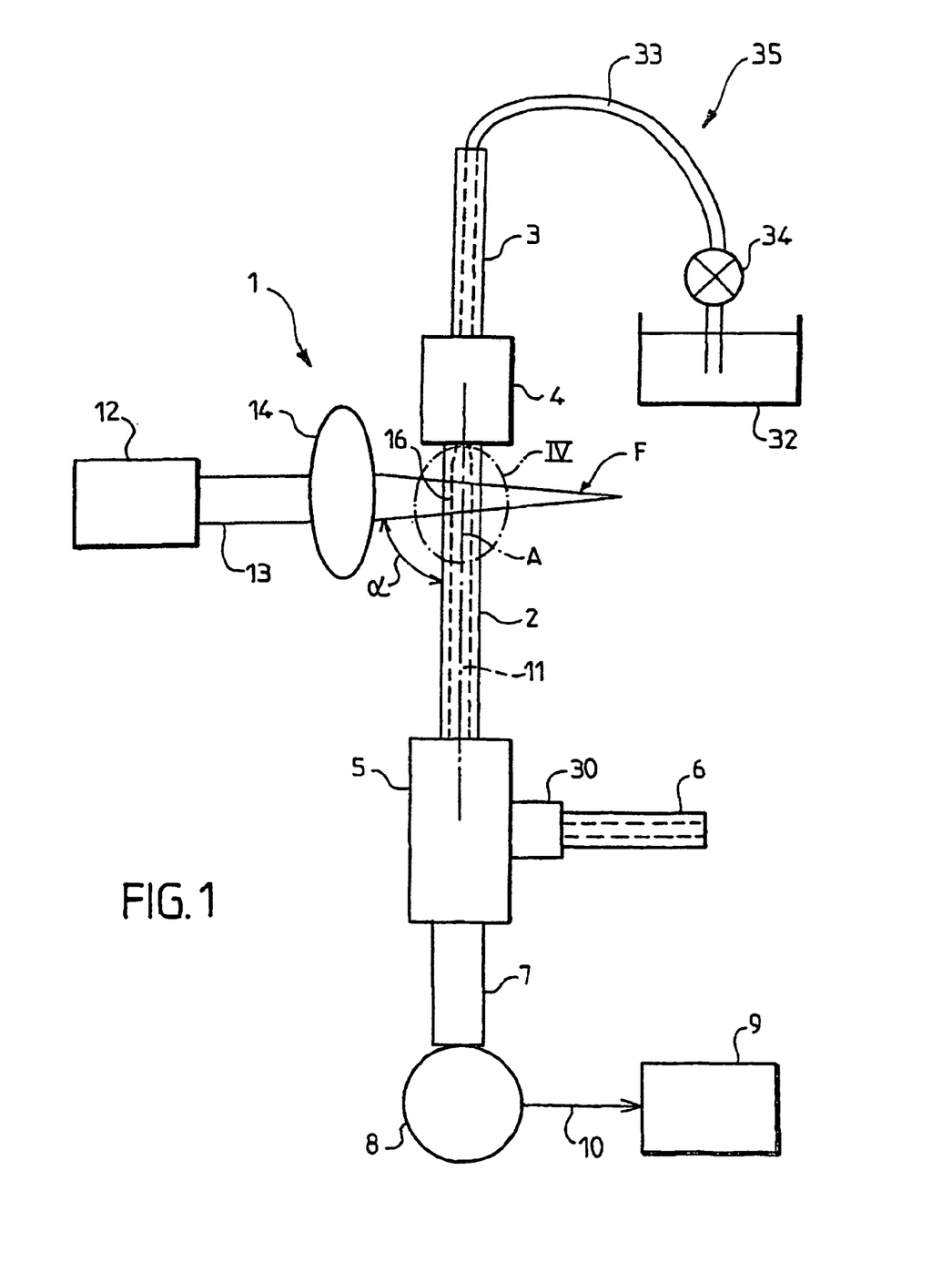
FIG. 1 is an overall schematic view of an analysis device according to a first embodiment of the invention.

In a first embodiment described with reference to FIG. 1, the analysis device, denoted overall by 1, comprises a tube 2 made of a polymer having a refractive index less than that of water, or made of silica (for example with a refractive index of 1.45 for a wavelength of 488 nm). The tube 2 is a tube through which a stream of a solution coming from a separation apparatus 35 flows via an output pipe 3 of this apparatus, which is for example a chromatography column, a PEEK tube or a steel tube of small cross section. The apparatus 35 is a high-performance liquid chromatography or micro- or nano-high-performance liquid chromatography separation apparatus of a type known to those skilled in the art and having, schematically, a main reservoir 32 tube the dissolved substances to be separated, a separation column 33 connected to the reservoir 32 and a pump 34 for making the solution flow through the separation column 33. The separation column is connected to the output pipe 3 or is coincident with the latter.

The tube 2 is fastened to the output pipe 3 in a rigid and contiguous manner by an opaque connecting sleeve 4 having no dead volume. Inside this sleeve, one end of the tube 2 butts against one end of the pipe 3. The solution contains one or more molecular substances which have been separated in the separation apparatus and which it is desired to detect and assay by fluorescence measurement.

A short portion 16 of the tube 2 is illuminated transversely and locally by a projection means comprising an excitation light source 12 emitting at least one wavelength chosen in order to induce a fluorescence reaction in at least one of the substances to be detected. In order to excite the fluorescence of several substances simultaneously, it is also possible to provide several projection means with excitation light sources having different wavelengths, these placed side by side along the tube 2 and/or around its periphery. In this case, the various substances will fluoresce at different wavelengths and it will be opportune to add, downstream of the collection means, a spectral separation system, of the optical filter, prism monochromator or diffraction grating type, allowing one or more emission wavelength bands to be selected. This will also be the case if the excitation source is a laser emitting in the UV, it then being possible for the various substances to each undergo specific native fluorescence.

The directed beam of excitation light 13 passes through a set of lenses 14 designed to make the beam F converge on the tube portion 16 so that the diameter of the beam F in the tube 2 is approximately equal to the internal diameter of the channel 11 of the tube 2. Thus, the loss of part of the excitation light not encountered by the solution is minimized, whereas the illuminated volume of solution remains sufficient to induce fluorescence light in a detectable amount right from the very low concentrations of fluorescent substance. The yield in converting excitation light into fluorescence light is therefore optimized, owing to the orthogonal geometry adopted.

The set of lenses 14 could also make the beam F diverge, for example if the source 12 produces a narrower beam 13 than the inside of the tube 2. The direction of incidence of the beam F makes an angle α of greater than 60°, and approximately 90° in the example shown, with the direction of the axis A of the tube 2.

Preferably, if the direction of incidence of the beam F with respect to the axis A is inclined, it is inclined so as to reduce the angle α between said direction of incidence and the axis A beside the collecting means 5, in order to orient the excitation light on the opposite side from the measurement means and thus reduce the excitation light scattering at the measurement means.

When the tube has a refractive index less than that of water, the fluorescence light generated locally in the illuminated portion 16 is guided along the axial direction of the tube 2 by successive reflections off its internal surface, the tube 2 forming a cylindrical wave guide with a liquid core.

Figure 4:
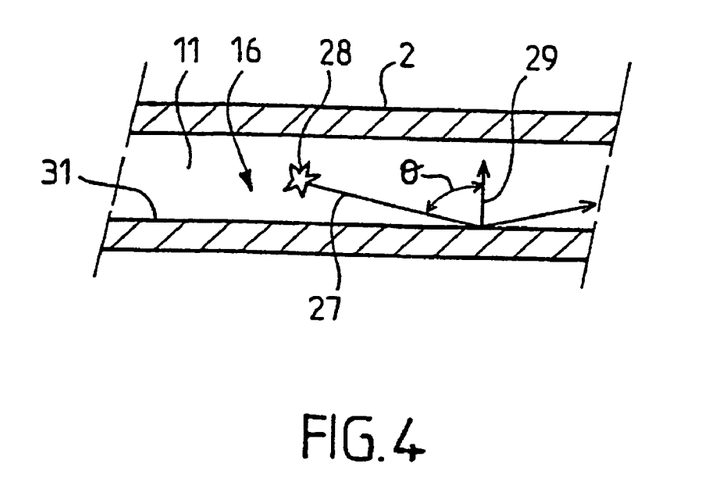
FIG. 4 is an enlarged view of a detail, circled at IV, of the device of FIG. 1.

FIG. 4 shows a fluorescence light ray 27 generated at a point 28 in the solution inside the channel 11, for a light ray having a sufficient angle of inclination to this interface. The angle of incidence of the ray 27 is determined by the angle θ between the ray 27 and the vector 29 pointing toward the inside of the tube 2 and perpendicular to the interface 31 between the solution, having a refractive index n', and the tube 2, having a refractive index n. The total reflection condition for the ray 27 is: $\theta \geq \arcsin(n/n')$. Thus, by choosing the material of the tube 2 for minimizing the refractive index n, the reflection coefficient at the interface 31 is high for most of the fluorescence light rays generated and equal to one for the rays that satisfy the abovementioned condition.

At the opposite end of the tube 2 from the separation system, an opaque, hollow T-connector 5 is fitted so as, on the one hand, to connect the tube 2 to one or more collecting optical fibers 7 placed along the extension of the tube 2 and, on the other hand, to connect the tube 2 to a discharge pipe 6 allowing the solution to flow from the tube 2 perpendicular thereto. At the center of the connector 5, the tube 2 butts against the collecting fiber 7 so as to minimize the loss of fluorescence light by scattering at the interface between them. The solution to be analyzed therefore flows through the tube 2 before re-emerging via the side branch 30 of the connector 5.

The optical fiber or fibers 7 axially collects or collect the emitted fluorescence light and guides (guide) it as far as a photo multiplier tube 8, or another type of optical detector. The photomultiplier tube 8 produces a measurement signal which is taken by a linking means 10 to a data processing system 9, for example a microcomputer, which includes software means known to those skilled in the art for processing the measurement signal received and for producing an analysis result, for example absolute or relative quantitative measurements of the concentration of the substance or substances emitting fluorescence light.

The internal channel 11 of the tube 2 has, at the end fitted into the sleeve 4, a conical, ellipsoidal or paraboloidal peripheral internal surface in order to increase the reflection of the fluorescence light in the direction of the collecting fibers 7, the tube then having an enlarged internal cross section compared with that of the pipe 3.

Because of the good optical transmission between the tube 2 and the collecting fiber 7, it is unnecessary for there to be spectral or spatial filtering means between the tube 2 and the optical detector, although it is also possible to provide such means in order to improve the detection thresholds. Although not shown, electrical supply means are incorporated into or connected to the photomultiplier tube 8 and to the light source 12 in order to operate them.

Figure 2:
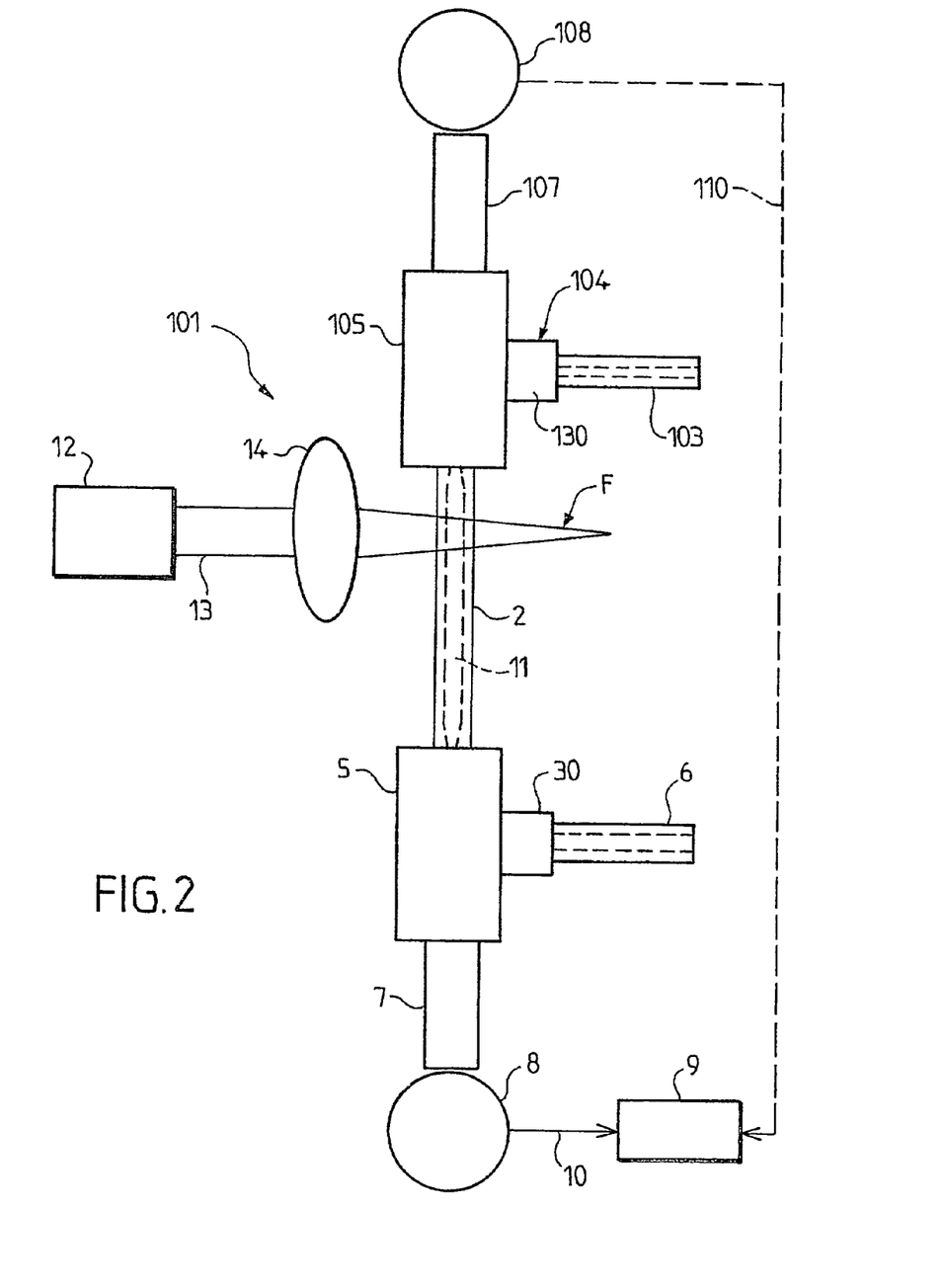
FIG. 2 is an overall schematic view of an alternative version of the device of FIG. 1.

In an alternative version of the first embodiment, shown in FIG. 2, the analysis device 101 includes, in place of the connecting sleeve 4, a second opaque hollow T-connector 105, identical or similar to the T-connector 5, which joins the tube 2, via a right-angled side branch 130 connected to a joining means 104, to the output pipe 103, similar to the pipe 3, and connects a second bundle 107 of collecting optical fibers, identical or similar to the fibers 7, lying along the extension of the tube 2, in order to guide fluorescence light as far as a second photomultiplier tube 108, identical or similar to the photomultiplier tube 8. The photomultiplier tube 108 may be connected via a line 110 to the aforementioned system 9. In this version, the arrangement at the two ends of the tube 2 is therefore symmetrical so as to collect all the fluorescence light trapped in the tube 2, whatever its direction of propagation. The solution enters the tube 2 via the pipe 103 and leaves via the discharge pipe 6. The other parts of the device 101 are identical or similar to those of the device 1 of FIG. 1. In this case, one end or both ends (as shown in FIG. 2) of the tube has or have a conical, ellipsoidal or paraboloidal wall.

Figure 3:
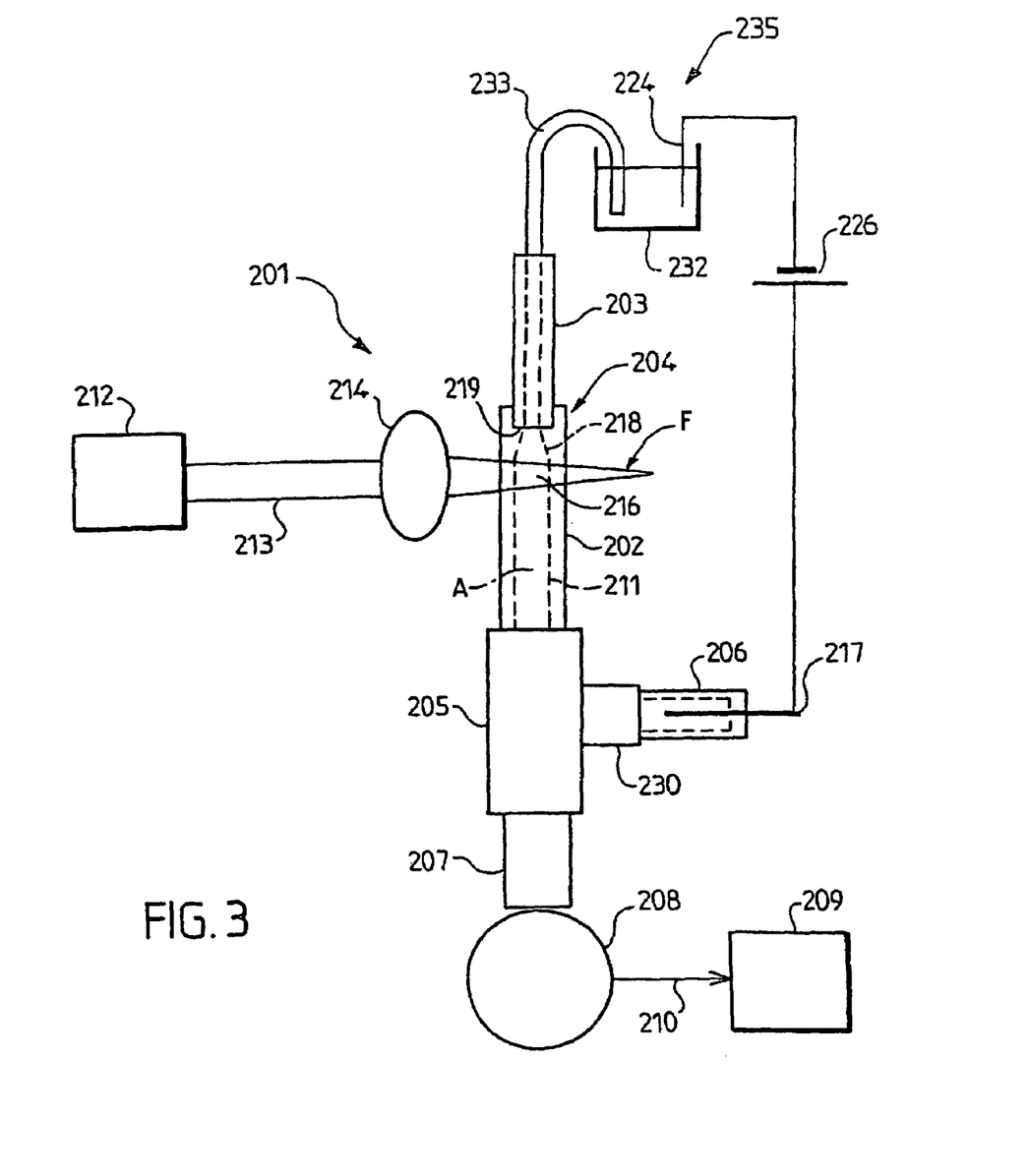
FIG. 3 is an overall schematic view of an analysis device according to a second embodiment of the invention.

A second embodiment of the invention will now be described with reference to FIG. 3, in which the elements identical or similar to those of the first embodiment bear the same reference numbers as in FIG. 1, increased by 200. The analysis device 201 is connected, in operation, to an electrophoretic separation system 235, for example one operating by capillary electrophoresis, isotachophoresis or electrochromatography, the output pipe 203 of which is a silica capillary or an electrophoretic separation tube. The solution is an electrolyte contained in the main reservoir 232 of the separation system 235, the pipe 203 connected to the reservoir 232 via a column 233, the tube 202 connected to the pipe 203, the inside of the T-connector 205 and a lateral buffer reservoir 206. The electrolyte is in electrical contact with a first electrode 224 of the separation system, immersed in the reservoir 232, and with a second electrode 217 inserted in a sealed manner through the wall of the buffer reservoir 206. For example, the reservoir 206 is in the form of a test tube, the open end of which is sealed into the side branch 230 of the connector 205 and the electrode 217 passes in a sealed manner through the bottom of said test tube. Of course, the reservoir 206 is subjected to atmospheric pressure via an appropriate aperture. There is thus electrical continuity parallel to the axis of the pipe 203 and of the tube 202 and, at the T-connector 205, perpendicular to the axis of the tube 202.

In operation, these electrodes are connected to a DC voltage source 226 of the separation system 235 allowing a potential drop to be established within the pipe 203 and the tube 202 for separating dissolved substances by electrophoresis. The junction 204 between the tube 202 and the pipe 203 is obtained by the latter fitting into the former, the inside diameter of the tube 202 being coincident with the outside diameter of the pipe 203. At this junction, the internal wall of the tube 202 has a frustoconical, or ellipsoidal or paraboloidal constriction whose face 218 allows the fluorescence light to be reflected toward the collecting fibers 207 so as to substantially increase the efficiency of collection of fluorescence light by the fibers 207. Greater performance may be obtained if the face 218 is coated with an oxidation-resistant reflective material 242, such as gold, silver or platinum, for example by thin-film deposition by vacuum evaporation (see FIG. 5). This constriction has, facing away from the inclined face 218, a shoulder 219 serving as a stop for that part of the pipe 203 fitted into the tube 202. To prevent the accumulation of contaminants at the junction, the interface between the tube 202 and the pipe 203 must be very uniform. This is obtained by having a good surface finish and a tight fit with adhesive bonding.

The operation of the analysis device 201 is similar to that of the device 1. The light source 212 and the set of lenses 214 direct the excitation light beam 213 on to a portion 216 of the tube 202. The portion 216 subjected to the local excitation illumination is preferably chosen to be adjacent to the frustoconical constriction and to the junction with the pipe 203, so as to reduce the dead volume and the influence of the variation in internal diameter of the separation tube formed by the pipe 203 and the tube 202. The photometric detector 208 transmits a measurement signal via the linking means 210 to the processing system 209.

The tube 2 or 202 has a large internal diameter, for example up to 200 μm for use in capillary electrophoresis or μ-HPLC and up to 1000 μm for use in HPLC, so as to optimize the illuminated volume of solution and, consequently, the fluorescence detection sensitivity.

The cylindrical shape of a capillary channel favors the propagation of the fluorescence emitted inside the capillary tube, provided that the refractive index of the propagation channel is higher than the index of the "outer" adjacent medium.

Propagation therefore takes place in the liquid stream contained in the capillary channel 2 if the latter is made of a polymer having an index less than that of water or of the commonly used solvents.

Figure 5:
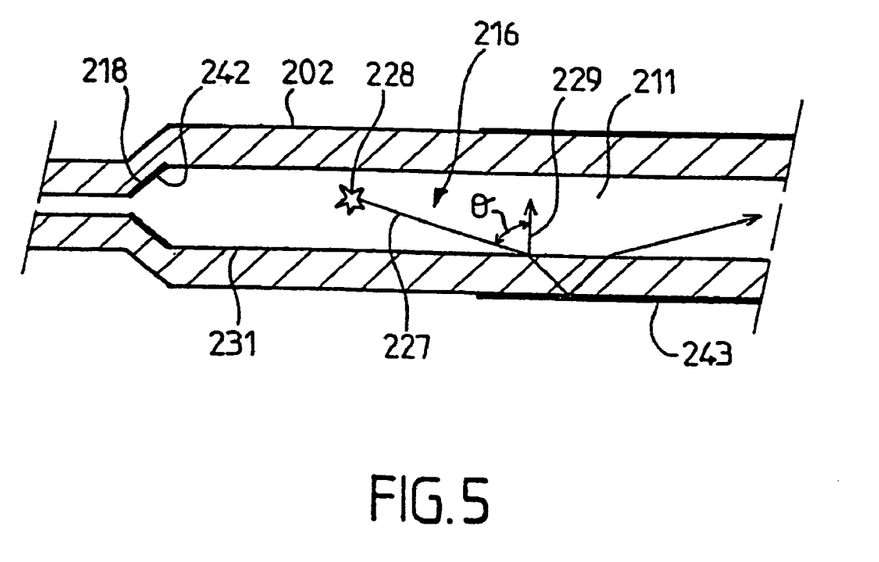
FIG. 5 is an enlarged view of a similar detail of the device of FIG. 3.

FIG. 5 shows a silica tube 202, having a refractive index n greater than that of water, with a fluorescence light ray 227 generated at a point 228 in the solution inside the channel 211. The angle of incidence of the ray 227 is determined by the angle θ between the ray 227 and the vector 229 pointing toward the inside of the tube 202 and perpendicular to the interface 231 between the solution, having a refractive index n', and the wall of the tube 202, having a refractive index n. Since n is greater than n', there will be, of course, total reflection of the ray 227 which propagates along the silica wall. Since this index n is greater than that n" of the air surrounding the tube 202, depending on the aforementioned angle of incidence and the chosen value of n, the ray is at least partly reflected, at the interface between the tube and the surrounding air, toward the inside of the wall and into the channel. Preferably, the index n" is less than the index n. No sleeve is necessary owing to the fact that the light is collected along the longitudinal axis.

As can be seen in FIGS. 4 and 5, one propagation direction is preferential here: for this, the capillary tube has an enlarged cross section constituting a detection cell 216 adjacent to the joining means 204. The enlarged region of conical, ellipsoidal or paraboloidal shape may also be coated, on the inside, with a reflective material, made of gold, silver or platinum, by a process such as thin-film deposition by vacuum evaporation. This widening of the capillary tube 202 at the excitation region 216 allows a larger sample volume to be irradiated.

The addition of a coating 243 acting as a mirror on the external wall of the capillary tube 202 makes it possible to reduce the critical angle θ (the angle relative to the vector 229) and thus decrease the fluorescence transmitted/scattered in the air surrounding the tube. However, this coating 243 must not cover the excitation region 216 of the detection cell, which must remain transparent to the beam F.

It is also possible to use a sleeve that has the same external reflective coating 243, into which sleeve are inserted and adjusted the separation capillary tube 203 and the wider capillary tube 202 serving as detection cell, preferably with adhesive bonding, thereby allowing this sleeve to be machined to the desired shape.

In order to maintain the electrophoretic and chromatographic resolutions, the excitation beam F may have a cross section of elliptical shape, the major axis of this ellipse being perpendicular to the longitudinal axis A of the capillary tube and the minor axis of this ellipse being parallel to said axis A.

Of course, the tube 2 may be made of silica and, conversely, the tube 212 may be made of a polymer without departing from the scope of the invention.

Although the invention has been described in relation to several particular embodiments, it is obvious that it is in no way limited thereby and that it comprises all technical equivalents of the means described and also their combinations, provided that these fall within the scope of the invention.

The invention claimed is:

1. A laser-induced fluorescence analysis device (1, 101, 201) comprising:
    a tube (2, 202) having a channel (11, 211) capable of containing a solution comprising at least one substance able to undergo a laser-induced fluorescence reaction, the material of said tube being substantially transparent to excitation light;
    at least one projection means (12, 14; 214, 212) capable of projecting an excitation light beam (13, 213) locally on a portion (16, 216) of said channel in a direction making an angle of greater than 60° to a longitudinal direction (A) of said channel, said excitation light being capable of inducing a fluorescence reaction in said substance or one of said substances;
    at least one optical collecting means (7, 107, 207) placed so as to collect fluorescence light from said channel;
    at least one optical measurement means (8, 108, 208) coupled to said collecting means so as to be able to measure said collected fluorescence light; and
    a processing means (9, 209) capable of processing a measurement signal transmitted by said measurement means in order to produce a result of the analysis of said solution; characterized in that a first collecting means (7, 207) is mechanically coupled to a first end of said tube (2, 202), said tube being made of a material whose refractive index is either less than that of water in the channel (11, 211) or greater than both that of water in the channel and that of the air surrounding the tube (2, 202), so as to be able to guide said fluorescence light along said channel in the channel and/or in the wall of the tube as far as said first collecting means, which collecting means is arranged so as to collect said fluorescence light propagating approximately along said longitudinal direction of the channel, and in that it includes a joining means (4, 104, 204) for connecting, in operation, a second end of said tube to an output pipe (3, 103, 203) of a separation system, so as to allow said solution to flow and/or said substance or substances in said solution to be transported between said separation system and said tube, said tube (2, 202) having, at said second end, an internal wall (218) of approximately conical, ellipsoidal or paraboloidal shape, one face of which is turned toward said first end and is capable of reflecting said fluorescence light toward said first end, said tube then having an internal cross section larger than that of said output pipe (3, 203) and constituting a fluorescence detection cell (16, 216).

2. The device as claimed in claim 1, characterized in that said tube portion (16, 216) locally illuminated by said excitation light beam is approximately adjacent to said joining means, so that said detection cell contains the region for exciting said substance or one of said substances.

3. The device as claimed in claim 1, characterized in that the second end of the tube has, facing away from said face (218), an internal shoulder (219) of cross section corresponding approximately to the external cross section of said output pipe and serving as a stop for that part of said output pipe (203) fitted into the tube (202).

4. The device as claimed in claim 3, characterized in that the internal cross section of said output pipe corresponds approximately to the internal cross section of the constriction defined between said shoulder and said face, at said second end of the tube.

5. The device as claimed in claim 1, characterized in that each collecting means comprises a waveguide (7, 107, 207), a hollow T-connector (5, 105, 205) being placed between said waveguide and the corresponding end of the tube in order to connect them, one in the extension of the other, a side branch (30, 130, 230) of said connector allowing said solution to flow and/or said substance or substances in solution to be transported toward or from the outside of said tube.

6. The device as claimed in claim 5, characterized in that said lateral branch (230) of a first T-connector (205) connects said first end of said tube to a reservoir (206), a first electrode (217) being placed through a wall of said reservoir so as to be in contact with said solution, said solution being electrically conducting and in contact with a second electrode (224) placed some distance from the first electrode, said electrodes being connected to a voltage source (226) so as to establish an electrical potential difference between the two ends of the tube (202) in order to make said substance or one of said substances migrate by electrophoresis, the waveguide (207) associated with said first collecting means being connected via said first connector to said first end in the extension of the tube.

7. The device as claimed in claim 5, characterized in that the side branch (130) of a second hollow T-connector (105) connects said second end of said tube to the aforementioned joining means (104), the waveguide (107) associated with a second collecting means being connected via said second T-connector to said second end of the tube in the extension of the latter.

8. The device as claimed in claim 7, characterized in that said tube (2) also has, at said first end, an internal wall of approximately conical, ellipsoidal or paraboloidal shape, one face of which is turned toward said second end and is capable of reflecting said fluorescence light toward said second end.

9. The device as claimed in claim 1, characterized in that the approximately conical (218), ellipsoidal or paraboloidal internal wall(s) of the tube (2, 202) is (are) coated with an oxidation-resistant reflective material (242).

10. The device as claimed in claim 1, characterized in that said tube (2, 202) has an internal diameter of up to 200 μm for use in capillary electrophoresis or μ-HPLC and up to 1000 μm for use in HPLC.

11. The device as claimed in claim 1, characterized in that said projection means comprises a light source (12, 212) placed laterally some distance from said channel and optical means (14, 214) placed between the light source and the channel in order to match the cross section of said excitation light beam to the inside diameter of said channel.

12. The device as claimed in claim 11, characterized in that the external wall of the tube is coated with a reflective material (243), with the exception in particular of the wall portion facing the excitation region (216) of the detection cell, which must remain transparent to the beam (F).

13. The device as claimed in claim 1, characterized in that the excitation beam (F) has a cross section of elliptical shape, the major axis of this ellipse being perpendicular to the longitudinal axis (A) of the tube and the minor axis of this ellipse being parallel to said longitudinal axis (A) of the tube.

14. A chromatographic or electrophoretic separation apparatus (35, 235), characterized in that it includes an analysis device (1, 101, 201) as claimed in claim 1.

15. The device as claimed in claim 2, characterized in that the second end of the tube has, facing away from said face (218), an internal shoulder (219) of cross section corresponding approximately to the external cross section of said output pipe and serving as a stop for that part of said output pipe (203) fitted into the tube (202).

16. The device as claimed in claim 6, characterized in that the side branch (130) of a second hollow T-connector (105) connects said second end of said tube to the aforementioned joining means (104), the waveguide (107) associated with a second collecting means being connected via said second T-connector to said second end of the tube in the extension of the latter.

* * * * *